United States Patent [19]

Berg

[11] Patent Number: 5,445,715
[45] Date of Patent: Aug. 29, 1995

[54] SEPARATION OF M-XYLENE FROM XYLENES BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 411,215

[22] Filed: Mar. 27, 1995

[51] Int. Cl.6 .............................. B01D 3/36; C07C 7/06
[52] U.S. Cl. ........................................ 203/50; 203/60; 203/57; 585/864; 585/866
[58] Field of Search ............................ 203/50, 60, 57; 585/866, 864

[56] References Cited

U.S. PATENT DOCUMENTS

| | | | |
|---|---|---|---|
| 2,456,561 | 12/1948 | Lake et al. | 203/60 |
| 2,532,031 | 11/1950 | Nixon et al. | 203/50 |
| 2,630,406 | 3/1953 | Linn | 203/50 |
| 2,957,811 | 10/1960 | Geiser | 203/60 |
| 5,039,380 | 8/1991 | Berg | 203/60 |

*Primary Examiner*—Wilbur Bascomb, Jr.

[57] ABSTRACT m-Xylene is very difficult to separate from mixtures of p-xylene and o-xylene by conventional distillation or rectification because of the proximity of their boiling points. m-Xylene can be readily separated from p-xylene and mixtures of p-xylene and o-xylene by azeotropic distillation. An effective agent is tetraethyl ortho silicate.

2 Claims, No Drawings

SEPARATION OF M-XYLENE FROM XYLENES BY AZEOTROPIC DISTILLATION

FIELD OF THE INVENTION

This invention relates to a method for separating m-xylene from xylenes using a certain organic liquid as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

p-Xylene, B.P.=138.4° C. and m-xylene, B.P.=139.1° C. have a relative volatility of only 1.02 and are virtually impossible to separate by conventional distillation or rectification. Azeotropic distillation would be an attractive method of effecting the separation of p-xylene from m-xylene if an agent can be found that (1) will enhance the relative volatility between p-xylene and m-xylene and (2) is easy to recover from the xylenes. The advantage of using azeotropic distillation in this separation can be seen from the data shown in Table 1. If an agent can be found that will increase the relative volatility to 1.5, 99% purity of m-xylene from p-xylene can be obtained with only 22 theoretical plates.

TABLE 1

| Effect Of Relative Volatility an Theoretical Stage Requirements | | | | | | | | |
|---|---|---|---|---|---|---|---|---|
| Separation Purity, | Relative Volatility | | | | | | | |
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

OBJECTIVE OF THE INVENTION

The object of this invention is to provide a process or method of azeotropic distillation that will enhance the relative volatility of m-xylene to xylenes in their separation in a rectification column. It is a further object of this invention to identify an organic compound azeotropic distillation agent that is stable and can be separated from the xylenes.

SUMMARY OF THE INVENTION

The objects of the invention are provided by a process for the separation of m-xylene from xylenes which entails the use of an organic compound which will enhance the relative volatility of m-xylene from xylenes when used as the azeotropic distillation agent.

DETAILED DESCRIPTION OF THE INVENTION

I have discovered that tetra ethyl ortho silicate will increase the relative volatility of m-xylene from p-xylene to a range of 1.5 to 1.6 and of m-xylene to o-xylene of 1.3 to 1.8.

THE USEFULNESS OF THE INVENTION

The usefulness or utility of this invention can be demonstrated by referring to the data presented in Table 1. Tetra ethyl ortho silicate can separate m-xylene from xylenes by azeotropic distillation and that the ease of separation as measured by relative volatility is in the range of 1.5 to 1.6 and of m-xylene to o-xylene of 1.3 to 1.8.

WORKING EXAMPLES

Example 1: 150 grams of p-xylene, 150 grams of m-xylene and 100 grams of tetra ethyl ortho silicate were placed in the stillpot of a 5.6 theoretical plate glass perforated plate rectification column and operated at total reflux for four hours. Analysis indicated a vapor composition of 54.6% p-xylene, 45.4% m-xylene; a liquid composition of 94.9% p-xylene, 5.1% m-xylene. This is a relative volatility of m-xylene to p-xylene of 1.62.

Example 2: 180 grams of p-xylene, 70 grams of m-xylene and 100 grams of tetra ethyl ortho silicate were placed in the stillpot of a 5.6 theoretical plate glass perforated plate rectification column and operated at total reflux for nine hours. Analysis indicated a vapor composition of 37.1% p-xylene, 62.9% m-xylene; a liquid composition of 84.7% p-xylene, 15.3% m-xylene. This is a relative volatility of m-xylene to p-xylene of 1.49.

Example 3: Fifteen grams of p-xylene, ten grams of m-xylene and five grams of o-xylene and thirty grams of tetra ethyl ortho silicate were charged to a vapor-liquid equilibrium still and refluxed for twelve hours. Analysis indicated a vapor composition of 56.4% p-xylene, 23.7% m-xylene, 19.9% o-xylene; a liquid composition of 71.7% p-xylene, 13.1% m-xylene, 15.2% o-xylene. This is a relative volatility of m-xylene to p-xylene of 2.3 and of m-xylene to o-xylene of 1.38.

Example 4: Twenty grams of p-xylene, six grams of m-xylene, four grams of o-xylene and forty grams of tetra ethyl ortho silicate were charged to a vapor-liquid equilibrium still and refluxed for five hours. Analysis indicated a vapor composition of 67.3% p-xylene, 19.3% m-xylene, 13.4% o-xylene; a liquid composition of 78.5% p-xylene, 12.3% m-xylene, 9.2% o-xylene. This is a relative volatility of m-xylene to p-xylene of 1.83 and of m-xylene to o-xylene of 1.09.

I claim:

1. A method for recovering m-xylene from a mixture of m-xylene and p-xylene which comprises distilling a mixture of m-xylene and p-xylene in the presence of an azeotrope forming agent, recovering the m-xylene and the azeotrope forming agent as overhead product and obtaining the p-xylene as bottoms product, wherein said azeotrope forming agent consists of tetra ethyl ortho silicate.

2. A method for recovering m-xylene from a mixture of m-xylene, p-xylene and o-xylene which comprises distilling a mixture of m-xylene, p-xylene and o-xylene in the presence of an azeotrope forming agent, recovering the m-xylene and the azeotrope forming agent as overhead product and obtaining the p-xylene and o-xylene as bottoms product, wherein said azeotrope forming agent consists of tetra ethyl ortho silicate.

* * * * *